United States Patent [19]

Engel et al.

[11] Patent Number: 5,798,234
[45] Date of Patent: Aug. 25, 1998

[54] METHOD FOR THE DIRECTED MODIFICATION OF ENZYMES, MODIFIED ENZYMES AND THEIR USE

[75] Inventors: Paul C. Engel; David Rice, both of Sheffield, Great Britain

[73] Assignee: Degussa Aktiengesellschaft, Germany

[21] Appl. No.: 831,753

[22] PCT Filed: Oct. 17, 1994

[86] PCT No.: PCT/EP94/03420

§ 371 Date: Apr. 17, 1996

§ 102(e) Date: Apr. 17, 1996

[87] PCT Pub. No.: WO95/11296

PCT Pub. Date: Apr. 27, 1995

Related U.S. Application Data

[63] Continuation of Ser. No. 628,699, Apr. 17, 1996, abandoned.

[30] Foreign Application Priority Data

Oct. 18, 1993 [DE] Germany ............... 43 35 448.3

[51] Int. Cl.[6] ............... C12P 13/00; C12P 7/40; C12N 15/00; C12N 9/02
[52] U.S. Cl. ............... 435/128; 435/136; 435/146; 435/172.1; 435/189; 435/190; 435/280
[58] Field of Search ............... 435/189, 190, 435/128, 136, 146, 172.1, 280

[56] References Cited

PUBLICATIONS

Kataoka et al: "Site–directed mutagenesis of a hexapeptide segment involved in substrate recognition of Phenylalanine Dehydrogenase from Thermoacetinomyces intermedius", J. Biochem., vol. 114, No. 1, Jul. 1993, pp. 69–75.

Wilks et al: "Designs for broad substrate specificity keto acid dehydrogenase", Biochemistry, vol. 29, No. 37, 1990, pp. 8587–8591.

Green et al: "Inversion of the substrate specificity of Yest Alcohol Dehydrogenase", J.Biochem., vol. 268, No. 11, Apr. 15, 1993, pp. 7792–7798.

Wilson et al: "Computational method for the design of enzymes with altered substrate specificity", J.MolBiol., vol. 220, 1991, pp. 495–506.

Power et al: Biotechnology, vol. 7b, "Gene Technology"; vol. eds. Jacobsen, G.K. & Jolly, S.O., chapter 6b: The Engineerying of structural and catalytic properties of proteins, pp. 2620276, VCH Publishers, ISBN 0–89573–561–X.

J.E. Rife and W.W. Cleland (1980) Biochemistry, 19, 2328–2333.

K.S. Lilley and P.C. Engel (1988) Biochemical society transactions, 16, 875–876.

*Primary Examiner*—Robert A. Wax
*Assistant Examiner*—Elizabeth Slobodyansky
*Attorney, Agent, or Firm*—Cushman Darby & Cushman IP Group of Pillsbury Madison & Sutro

[57] ABSTRACT

Enzymes with modified substrate specificity and methods of obtaining same by the steps of a) determining the structure of two or more enzymes in the same group, b) comparing the structure of the substrate binding sites of the enzymes, and c) modifying selected amino acids by genetic mutation so that the substrate preference of one of the enzymes is altered. The methods are particularly useful for the stereospecific interconversion of oxyacids and aminoacids.

7 Claims, No Drawings

METHOD FOR THE DIRECTED MODIFICATION OF ENZYMES, MODIFIED ENZYMES AND THEIR USE

This is a continuation of application Ser. No. 08/628,699, filed on Apr. 17, 1996, which was abandoned upon the filing hereof which claims benefit of international application PCT/EP94/03420, filed Oct. 17, 1994.

BACKGROUND OF THE INVENTION

1. Field of the Invention

The invention is relative to a method for the directed modification of enzymes, modified enzymes and their use.

2. Background Information

Enzymes can usually be modified either by chemical modification of the amino acids forming the enzyme or by mutation of the gene coding the enzyme. Chemical modifications are frequently non-specific, so that the directed modifying of the enzyme structure by directed mutation of the gene has advantages over the chemical modification.

Modified enzymes frequently exhibit improved properties as regards activity, specificity or stability in comparison to the unmodified enzymes. Previous activities in this area were frequently limited to improving global properties of the enzyme such as e.g. stability vis-à-vis reaction media. Thus, for example, alkaline proteases were stabilized against the oxidizing action of bleaching agents. However, the problem of changing the specificity of enzymes in order to convert previously defined substrates has hardly been treated. One exception is the work of H. M. Wilks et al. (H. M. Wilks et al., Science 1988, 242, 1541–1544) in which the substrate specificity of a lactate dehydrogenase with lactate as preferred substrate is transformed to a malate dehydrogenase with malate as preferred substrate.

The selectivity for producing enantiomerically pure compounds is especially desirable for enzymes. The enantioselectivity is especially prominent in the case of amino-acid dehydrogenases, among others. Thus, amino-acid dehydrogenases were screened from a number of organisms. The most important enzymes for use in organic synthesis are alanine dehydrogenase (AlaDH, E.C. 1.4.1.1.), phenylalanine dehydrogenase (PheDH; still no E.C. number) and, especially, leucine dehydrogenase (LeuDH, E.C. 1.4.1.9.). However, the best-investigated enzyme of the group is the ubiquitous glutamate dehydrogenase (GluDH, E.C. 1.4.1.2.–4.), which forms an important branch point between carbon metabolism and nitrogen metabolism. GluDH catalyses the NAD (P)$^+$-dependent, oxidative deamination of L-glutamate to 2-oxoglutarate and ammonia:

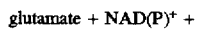

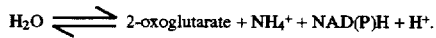

Amino-acid dehydrogenases generally catalyze the reversible reductive amination of prochiral keto acids to L-amino acids ((S) configuration) and the reverse reaction of the oxidative deamination of L-amino acids to oxo acids.

In most instances, including all NAD$^+$-dependent GluDH'es, the enzyme has six identical subunits of approximately 48 kD each. A considerable homology is found in the polypeptide chain of the hexameric GluDH'es; in particular, the glutamate binding pocket and the active center display a remarkable similarity (Britton, K. L., Baker, P. J., Rice, D. W. and Stillman, T. J., Eur. J. Biochem. 1992, 209, 851–859).

The degree of similarity between the structures of the members of the family of amino-acid dehydrogenases from different organisms is so great that a single superfamily of enzymes is assumed in the case of amino-acid dehydrogenases, which superfamily was produced by divergent evolution (S. Nagata, K. Tanisawa, N. Esaki, Y. Sakamoto, T. Ohshima, H. Tanaka and K. Soda, Biochemistry 1988, 27, 9056–62; H. Takada, T. Yoshimura, T. Ohshima, N. Esaki and K. Soda, J. Biochem. 1991, 109, 371–6).

The three-dimensional structure of the glutamate dehydrogenase from *Clostridium symbiosum* is known (Baker, P. J. et al., Proteins 1992, 12, 75–86). The gene of this enzyme was cloned and overexpressed in *Escherichia coli* (Teller, J. K. et al., Eur. J. Biochem. 1992, 286, 151–159). However, it has not been successful in the past to modify the enzymatic structure in such a manner by directed mutation of the gene that even certain substrates selected before the mutation were converted.

SUMMARY OF THE INVENTION

The invention therefore has the problem of making available a method for the directed modification of enzymes in which desired substrates can be converted independently of the natural substrate specificity of the enzyme. A further object of the invention is to indicate a modified enzyme which is altered at its substrate binding site so that a desired substrate which is generally not preferred is converted by the modified enzyme with sufficient activity, selectivity and stability.

This method solves the problem of the invention by carrying out in succession the steps indicated in claim 1. As a result of the fact that:

The structure of at least two enzymes from a group of enzymes is elucidated,

The binding pockets of the enzymes with elucidated structure from a group are compared, The amino acids are determined which are necessary for the binding of a substrate preferred for the unmodified enzyme, The amino acids in the binding pocket of the unmodified enzyme with elucidated structure are selected, which are to be modified for the binding of a desired substrate not preferred by the unmodified enzyme, The selected amino acids are modified by the mutation of a gene belonging to the enzyme, and The mutated gene is expressed and the purposefully modified enzyme isolated, it is possible to expand the substrate spectrum to new target structures vis-à-vis the unmodified enzyme. As a result thereof, an advantageous activity, selectivity or stability can be expanded to a larger number of substrates.

According to the invention the term "a group of enzymes" denotes all members of a sub-subclass according to E.C. nomenclature (E.C.=Enzyme Commission). The type of sub-subclass is not subject to any particular limitation. The preferred sub-subclasses include NAD (P)$^+$-dependent redox reactions with amines (group 1.4.1. according to E.C. nomenclature), serine proteases (group 3.4.21. according to E.C. nomenclature) and carboxylester hydrolases (group 3.1.1. according to E.C. nomenclature).

Within the framework of the invention the term "structural elucidation" denotes the determination of the spatial structure of an enzyme. It is basically necessary to obtain information about the structure of two enzymes from a group. All methods known to the expert in the art for the structural elucidation of enzymes can be used with advantage thereby for the method of the invention. It is especially preferable if the analysis of the amino-acid sequence is carried out for at least one enzyme of a group, an associated enzyme substrate complex is crystallized thereby and the spatial structure of the enzyme substrate complex elucidated. If the sequence of a second enzyme of the group is highly homologous to the structure of the first one, this is sufficient as regards the structure of the second enzyme of the group as information for carrying out the modifications on the enzyme. The term "highly homologous" denotes in this connection an at least 50% agreement of the sequence of two enzymes.

In the second step of the method of the invention the binding pockets of the enzymes of a group whose structure was elucidated in the first step of the method of the invention are compared with each other. The term "binding pocket" denotes in this connection the three-dimensional surroundings of the binding site of a substrate on the enzyme for the final purpose of conversion by the enzyme; the binding pocket is formed from amino acids which do not necessarily lie adjacent to each other in the sequence of the enzyme. When comparing the binding pockets of the enzymes, the influence of the individual amino acids of the binding pockets is tested as regards analogy for polarity, charge and steric demand on the substrate.

Then, taking into consideration the result obtainable in the analogy testing, the amino acids are determined which are necessary for the binding of a substrate preferred for the enzyme. The position of these amino acids in the sequence is also determined. This is then followed by the selection of those amino acids in the binding pocket of enzymes with elucidated structure which are to be modified for the binding of a desired substrate not preferred by the unmodified enzyme. The amino acids selected are preferably modified in such a manner by mutation of the corresponding triplet of the associated gene that the modified triplet codes the amino acid necessary for binding the desired substrate. The mutated gene is expressed in a suitable organism, the modified enzyme isolated from the organism and tested for the binding of the desired substrate as well as for activity, selectivity and stability.

It is advantageous to use a newly developed technology in this connection for testing the modified enzymes. For the screening and optimizing of the mutants the testing is carried out on microtiter plates which permit the testing of many mutants (in rows) on many substrates (lines). In the case of group 1.4.1. of the amino-acid dehydrogenases the oxidative deamidization is used as screening reaction; to this end the reactants (amino acid and cofactor) are brought together with an artificial electron acceptor as mediator (phenazine methosulfate) as well as with a colored terminal electron acceptor (tetrazolium dye). The activity of a mutated enzyme is indicated by a coloring.

The method of the invention has proven to be especially useful if amino-acid dehydrogenases of group 1.4.1 are used as enzymes and 2-oxo acids differing only in their group are used as substrates preferred both by the unmodified enzyme and by the modified enzyme. It was found in this manner that in the case of glutamate dehydrogenase from *Clostridium symbiosum* the following amino acids of the sequence of the enzyme exert a particular influence in the binding of the substrate: Valine 377, serine 380, threonine 193, lysine 89 and alanine 163; it was furthermore found that the following amino acids exert an additional influence: glutamine 110, aspartate 114, methionine 121 and arginine 205.

According to the method, a binding pocket with the groups valine 377, serine 380, threonine 193, lysine 89 and alanine 163 is then modified by mutating a gene belonging to the enzyme in order to produce enzymes for the stereospecific, reversible reaction of the oxidative deamination of an L-amino acid or reductive amination of an oxo acid in the case of an enzyme from the group with the E.C. number 1.4.1.

The invention also makes novel enzymes available. These enzymes preferably have a binding pocket which is modified at least in respect to one group in such a manner that a desired substrate which is not preferred by the unmodified enzyme is converted with sufficient activity, selectivity and stability. It is advantageous, especially for the binding of a substrate which is not preferred by the unmodified enzyme and is for the stereospecific reaction of the oxidative deamination of an L-amino acid or reductive amination of an oxo acid if the binding pocket displays at least one modification on the groups valine 377, serine 380, threonine 193, lysine 89 and alanine 163 with the consequence that the desired substrate can be bound and converted in an improved fashion by the modified enzyme.

Among other things, 2-oxo acids can be converted in high enantiomeric yield for the production of L-alpha-amino acids with the method of the invention and with the novel enzymes modified in accordance with the invention.

It is also advantageous to use the enzymes modified at least as regards one group in the binding pocket for converting L-alpha-amino acids for the production of 2-oxo acids. Moreover, it is highly advantageous to use the modified enzymes for converting DL-alpha-amino acids in order to product 2-oxo acids and D-alpha-amino acids.

The use of DL-alpha-amino acids as substrates makes enantiomerically pure D-amino acids accessible after conversion with enzymes of group 1.4.1. Economical L-alpha-amino acids can thus be reacted under extremely advantageous conditions to oxo acids.

DETAILED DESCRIPTION OF THE INVENTION

EXAMPLE 1

The three-dimensional crystalline structure of glutamate dehydrogenase from *Clostridium symbiosum* is known from the literature both as a complex with glutamate (T. J. Stillman et al., J. Mol. Biol., 1993, 234, pp. 1131–1139) and also in free form as well as a complex with the cofactor $NAD^+$ (P. J. Baker et al., Proteins, 1992, 12, pp. 75–86).

It is also known from the literature that the substrate specificity of glutamate dehydrogenase from *Clostridium symbiosum* stems from interactions with the side chains of the amino acids Lys 89, Ser 380, Gly 90, Ala 163 and Val 377 (T. J. Stillman et al., J. Mol. Biol., 1993, 234, pp. 1131–1139; the numeric designation of the amino acids refers to the position of the particular amino acid in the sequence of glutamate dehydrogenase from *Clostridium symbiosum*, calculated from the N terminal).

The specific interaction with the γ-carboxyl group of the glutamate substrate is exerted by the lysine pendant group in position 89 of the glutamate dehydrogenase from Clostridium symbiosum (K. L. Britton et al., J. Mol. Biol., 1993, 234, pp. 938–945).

A replacement of this side chain in position 89 by an uncharged and non-polar group therefore drastically reduces the activity of glutamate dehydrogenase from *Clostridium symbiosum* vis-à-vis glutamate and the activity vis-à-vis non-polar amino acids increases.

The wild type of glutamate dehydrogenase from *Clostridium symbiosum* is specific as concerns glutamate as substrate: At pH 7.0 and 25° C. in 0.1 molar phosphate buffer, with 1 mmole/l NAD$^+$ and 40 mmoles/l amino acid, the specificity constant $k_{cat}/K_M$ with L-glutamate as substrate was able to be determined at $5.1 \cdot 10^3$ l·mole$^{-1}$·s$^{-1}$ and an activity of 11.2 U/mg, whereas L-norleucine and L-methionine display no measurable activity under the same conditions (activity<$10^{-4}$ U/mg).

The gene coding the glutamate dehydrogenase from *Clostridium symbiosum* was point-specifically mutated by using mismatch oligonucleotide primers and subsequently selected according to the uracil DNA method for mutated DNA, both as described in Kunkel T. A. et al., Proc. Nat. Acad. Sci., 1985, 82, pp. 488–492 and in Kunkel T. A. et al., Methods in Enzymology, 1987, 154, pp. 367–382, cloned with the polymerase chain reaction, the DNA sequence analysis carried out and expression in *Escherichia coli* performed (J. K. Teller et al., Eur. J. Biochem., 1992, 206, pp. 151 to 159).

The enzyme expressed in *Escherichia coli* was immobilized on sepharose 6B by chromatography on remazol brilliant red GG as described in Syed S. E. H et al., Biochim. Biophys. Acta, 1990, 1115, pp. 123–130, isolated and, as described in T. J. Stillman et al. (J. Mol. Biol., 1993, 234, pp. 1131–1139), crystallized and subjected to X-ray structural analysis.

Result:

The glutamate dehydrogenase from *Clostridium symbiosum* in position 89 was modified by the above-described procedure by directed mutagenesis from lysine to leucine (Lys89Leu, K89L). In the case of the enzyme modified in position 89 in the sequence the activities with the same substrates as in the case of the wild type were determined.

The following relative activities (U/mg) were measured hereby under the same assay conditions as above:

|  | rel. activity (U/mg) |
|---|---|
| L-glutamate | 0.001 |
| L-norleucine | 0.012 |
| L-methionine | 0.005 |

Thus, whereas the wild type of glutamate dehydrogenase from *Clostridium symbiosum* only converts glutamate but not norleucine or methionine, the enzyme Lys 89 Leu (K89L) mutated in position 89 converts the three amino acids norleucine, glutamate and methionine in a ratio of $k_{cat}/K_M$ values of 1.2:1.1:0.5 U/mg.

EXAMPLE 2

The three-dimensional crystalline structure of glutamate dehydrogenase from *Clostridium symbiosum* is known from the literature both as a complex with glutamate (T. J. Stillman et al., J. Mol. Biol., 1993, 234, pp. 1131–1139) and also in free form as well as a complex with the cofactor NAD$^+$ (P. J. Baker et al., Proteins, 1992, 12, pp. 75–86).

It is also known from the literature that the substrate specificity of glutamate dehydrogenase from *Clostridium symbiosum* stems from interactions with the side chains of the amino acids Lys 89, Ser 380, Gly 90, Ala 163 and Val 377 (T. J. Stillman et al., J. Mol. Biol., 1993, 234, pp. 1131–1139; the numeric designation of the amino acids refers to the position of the particular amino acid in the sequence of glutamate dehydrogenase from *Clostridium symbiosum*, calculated from the N terminal).

By means of an additional comparison of the amino-acid sequences, known in the literature (K. L. Britton et al., J. Mol. Biol., 1993, 234, pp. 938–945), of the four amino-acid dehydrogenases Glutamate dehydrogenase from *Clostridium symbiosum*, Leucine dehydrogenase from *Bacillus stearothermophilus*, Phenylalanine dehydrogenase from *Thermoactinomyces intermedius* and Phenylalanine dehydrogenase from *Bacillus sphaericus* the groups Leu 89, Gly 90, Ala 163, Val 377 and Val 380 in the amino-acid sequence of leucine dehydrogenase were recognized as decisive for the substrate specificity (K. L. Britton et al., J. Mol. Biol., 1993, 234, pp. 943 and 944). Likewise, the groups Leu 89, Gly 90, gly 163, Leu 377 and Val 380 in the amino-acid sequence of phenylalanine dehydrogenase were recognized as decisive for the substrate specificity (K. L. Britton et al., J. Mol. Biol., 1993, 234, pp. 943 and 944). The numbering of the position of the amino acids always refers here to the numeric position of the particular amino acid in the sequence of glutamate dehydrogenase from *Clostridium symbiosum*.

However, since the substrate specificity of leucine dehydrogenase and phenylalanine dehydrogenase is totally different (K. L. Britton et al., J. Mol. Biol., 1993, 234, pp. 943 and 944) the substrate specificity of phenylalanine dehydrogenase from *Bacillus sphaericus* is altered by mutation of the groups Gly 163 and Leu 377 and modified in the direction of the substrate specificity of a leucine dehydrogenase.

The gene coding the phenylalanine dehydrogenase from *Bacillus sphaericus* was point-specifically mutated by using mismatch oligonucleotide primers and subsequently selected according to the uracil DNA method for mutated DNA, both as described in Kunkel T. A. et al., Proc. Nat. Acad. Sci., 1985, 82, pp. 488–492 and in Kunkel T. A. et al., Methods in Enzymology, 1987, 154, pp. 367–382, cloned with the polymerase chain reaction, the DNA sequence analysis carried out and expression in *Escherichia coli* performed (J. K. Teller et al., Eur. J. Biochem., 1992, 206, pp. 151 to 159).

The enzyme expressed in *Escherichia coli* T61 was purified as described in Syed S. Y. K. et al., FEBS Letters 370 (1995), 93–96.

Result:

The phenylalanine dehydrogenase from *Bacillus sphaericus* was modified by the above-described procedure in two positions in the amino-acid sequence: Instead of the amino acids Gly 163 and Leu 377 the mutated enzyme exhibited the amino acids Ala 163 and Val 377 at the corresponding location in the sequence. In the case of the enzyme modified in two positions in the sequence the activities were determined with different potential substrates under assay conditions like those in Y. Asano et al. (J. Biol. chem. 1987, 262, pp. 10346–10354) at pH 10.4 and 25° C. in 0.1 molar glycine NaOH buffer with 2.5 mmoles/l NAD$^+$ and 10 mmoles/l L-amino acid. The results are as follows:

| Amino acid | Wild type | mutant |
|---|---|---|
| L-Leu | 1.5% | 3.0% |
| L-Val | 1.7% | 6.4% |
| L-Met | 2.6% | 3.8% |
| L-Nva | 2.9% | 3.2% |

-continued

| Amino acid | Wild type | mutant |
|---|---|---|
| L-Ile | 1.0% | 5.5% |
| L-Phe (for comparison) | 100.0% | 7.7% |

The Phe activity of the wild type corresponds to 87.6 U/mg protein, measured under the same assay conditions as in Y. Asano et al. (J. Biol. Chem., 1987, 262, pp. 10346–10354) at pH 10.4 and 25° C. in 0.1 molar glycine NaOH buffer with 2.5 mmoles/l 1 NAD⁺ and 10 mmoles/l L-amino acid.

It can therefore be determined that not only the relative activity of the mutant in the case of the aliphatic L-amino acids comes close to the activity vis-à-vis L-phenylalanine but that the absolute activity of the mutant vis-à-vis aliphatic L-amino acids is greater than the activity of the wild type vis-à-vis these substrates. This means that the specificity has been significantly modified toward that of a leucine dehydrogenase.

EXAMPLE 3

0.4 mmoles (0.52 g) 2-ketocaproate (=2-oxonorleucine) was dissolved in 100 ml 0.1 molar phosphate buffer with pH 7 and 0.05 mole (2.68 g) ammonium chloride as well as 0.1 mmole (66.3 mg) $NAD^+$ added. Then, 4.5 mg of a glutamate dehydrogenase modified in position 89 from lysine to leucine were added and allowed to react under magnetic stirring. The measured activity of the enzyme modified in position 89 was 1.3 U/mg. After 96 hours 100 ml ethanol were added to the batch and the batch evaporated to low bulk on a rotary evaporator. The precipitated product was washed once with 10 ml cold water and once with ethanol and dried at 50° C. in a vacuum. The enantiomeric purity was determined by GC over chirasil-Val.

Yield of L-norleucine: 0.41 g (78% of theory)
Enantiomeric purity: >99.8% L-amount Further embodiments of the invention will become apparent from the following patent claims.

What is claimed is:

1. A method of modifying substrate specificity of an amino acid dehydrogenase from the group with E.C. number 1.4.1, wherein said dehydrogenase catalyzes the stereospecific, reversible reaction of oxidative deamination of an L-amino acid or reductive amination of an oxo acid and wherein said dehydrogenase has a binding pocket comprising amino acid residues corresponding to valine 377, serine 380, threonine 193, lysine 89 and alanine 163 of SEQ ID NO:1, said method comprising the steps of:

i) comparing the amino acid sequence of the amino acid dehydrogenase with the amino acid sequence of a second amino acid dehydrogenase from the group with E.C number 1.4.1; and ii) substituting one or more residues selected from the group consisting of valine 377, serine 380, threonine 193, lysine 89 and alanine 163 of SEQ ID NO:1 with the amino acid residues at corresponding positions in the second amino acid dehydrogenase by mutation of a gene encoding first amino acid dehydrogenase.

2. A method of modifying substrate specificity of an amino acid dehydrogenase from the group with E.C. number 1.4.1, wherein said dehydrogenase catalyzes the stereospecific, reversible reaction of oxidative deamination of an L-amino acid or reduction amination of an oxo acid and wherein said dehydrogenase has a binding pocket comprising amino acid residues corresponding to valine 377, serine 380, threonine 193, lysine 89, alanine 163, glutamine 110, aspartate 114, methionine 121, and arginine 205 of SEQ ID NO:1, said method comprising the steps of:

i) comparing the amino acid sequence of the amino acid dehydrogenase with the amino acid sequence of a second amino acid dehydrogenase from the group with E.C. number 1.4.1; and ii) substituting one or more residues selected from the group consisting of valine 377, serine 380, threonine 193, lysine 89, alanine 163, glutamine 110, aspartate 114, methionine 121, and arginine 205 of SEQ ID NO:1 with the amino acid residues at corresponding positions in the second amino acid dehydrogenase by mutation of a gene encoding first amino acid dehydrogenase.

3. A modified enzyme from the group with E.C. number 1.4.1, said enzyme having at least one binding pocket for the binding of a substrate for the stereospecific, reversible reaction of oxidative deamination of an L-amino acid or reductive amination of an oxo acid, said binding pocket comprising at least one modified residue selected from the group consisting of valine 377, serine 380, threonine 193, lysine 89 and alanine 163 of SEQ ID NO:1 belonging to the binding pocket of the unmodified enzyme.

4. The enzyme according to claim 3, wherein said binding pocket additionally comprises the groups glutamine 110, aspartate 114, methionine 121, and arginine 205 of SEQ ID NO:1.

5. A method of producing an L-alpha amino acid, said method comprising reacting a 2-oxo acid with an enzyme according to one of claims 3 or 4.

6. A method of producing a 2-oxo acid, said method comprising reacting an L-alpha amino acid with an enzyme according to one of claims 3 or 4.

7. A method of producing a mixture comprising a 2-oxo acid and a D-alpha amino acid, said method comprising reacting a DL-alpha amino acid with an enzyme according to one of claims 3 or 4.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 449 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Clostridium symbiosum ( x i ) SEQUENCE DESCRIPTION: SEQ ID NO:1:

```
Ser Lys Tyr Val Asp Arg Val Ile Ala Glu Val Glu Lys Lys Tyr Ala
 1               5                  10                  15

Asp Glu Pro Glu Phe Val Gln Thr Val Glu Glu Val Leu Ser Ser Leu
                20                  25                  30

Gly Pro Val Val Asp Ala His Pro Glu Tyr Glu Glu Val Ala Leu Leu
                35                  40                  45

Glu Arg Met Val Ile Pro Glu Arg Val Ile Glu Phe Arg Val Pro Trp
    50                  55                  60

Glu Asp Asp Asn Gly Lys Val His Val Asn Thr Gly Tyr Arg Val Gln
65                      70              75                  80

Phe Asn Gly Ala Ile Gly Pro Tyr Lys Gly Gly Leu Arg Phe Ala Pro
                    85                  90                  95

Ser Val Asn Leu Ser Ile Met Lys Phe Leu Gly Phe Glu Gln Ala Phe
                100                 105                 110

Lys Asp Ser Leu Thr Thr Leu Pro Met Gly Gly Ala Lys Gly Gly Ser
            115                 120                 125

Asp Phe Asp Pro Asn Gly Lys Ser Asp Arg Glu Val Met Arg Phe Cys
        130                 135                 140
```

-continued

```
Gln Ala Phe Met Thr Glu Leu Tyr Arg His Ile Gly Pro Asp Ile Asp
145             150             155             160

Val Pro Ala Gly Asp Leu Gly Val Gly Ala Arg Glu Ile Gly Tyr Met
            165             170             175

Tyr Gly Gln Tyr Arg Lys Ile Val Gly Gly Phe Tyr Asn Gly Val Leu
            180             185             190

Thr Gly Lys Ala Arg Ser Phe Gly Gly Ser Leu Val Arg Pro Glu Ala
        195             200             205

Thr Gly Tyr Gly Ser Val Tyr Tyr Val Glu Ala Val Met Lys His Glu
    210             215             220

Asn Asp Thr Leu Val Gly Lys Thr Val Ala Leu Ala Gly Phe Gly Asn
225             230             235             240

Val Ala Trp Gly Ala Ala Lys Lys Leu Ala Glu Leu Gly Ala Lys Ala
            245             250             255

Val Thr Leu Ser Gly Pro Asp Gly Tyr Ile Tyr Asp Pro Glu Gly Ile
        260             265             270

Thr Thr Glu Glu Lys Ile Asn Tyr Met Leu Glu Met Arg Ala Ser Gly
        275             280             285

Arg Asn Lys Val Gln Asp Tyr Ala Asp Lys Phe Gly Val Gln Phe Phe
    290             295             300

Pro Gly Glu Lys Pro Trp Gly Gln Lys Val Asp Ile Ile Met Pro Cys
305             310             315             320

Ala Thr Gln Asn Asp Val Asp Leu Glu Gln Ala Lys Lys Ile Val Ala
            325             330             335

Asn Asn Val Lys Tyr Tyr Ile Glu Val Ala Asn Met Pro Thr Thr Asn
        340             345             350

Glu Ala Leu Arg Phe Leu Met Gln Gln Pro Asn Met Val Val Ala Pro
        355             360             365

Ser Lys Ala Val Asn Ala Gly Gly Val Leu Val Ser Gly Phe Glu Met
    370             375             380

Ser Gln Asn Ser Glu Arg Leu Ser Trp Thr Ala Glu Glu Val Asp Ser
385             390             395             400

Lys Leu His Gln Val Met Thr Asp Ile His Asp Gly Ser Ala Ala Ala
            405             410             415

Ala Glu Arg Tyr Gly Leu Gly Tyr Asn Leu Val Ala Gly Ala Asn Ile
        420             425             430

Val Gly Phe Gln Lys Ile Ala Asp Ala Met Met Ala Gln Gly Ile Ala
        435             440             445

Trp
```